United States Patent [19]

Wuttke

[11] Patent Number: 5,714,650
[45] Date of Patent: Feb. 3, 1998

US005714650A

[54] CONTINUOUS MANUFACTURE OF 1,1-DIFLUOROETHANE

[75] Inventor: Klaus Guenter Wuttke, Wilmington, Del.

[73] Assignee: E. I. Du Pont de Nemours and Company, Wilmington, Del.

[21] Appl. No.: 474,884

[22] Filed: Jun. 7, 1995

[51] Int. Cl.$^6$ ................................. C07C 17/087
[52] U.S. Cl. ................. 570/165; 570/164; 570/166; 570/167; 570/168
[58] Field of Search ................. 570/164, 165, 570/166, 167, 168

[56] References Cited

U.S. PATENT DOCUMENTS

| | | | |
|---|---|---|---|
| 2,495,407 | 1/1950 | Chapman et al. | 260/653 |
| 3,190,930 | 6/1965 | Brock et al. | 260/653.6 |
| 3,862,995 | 1/1975 | Martens et al. | 200/653.6 |
| 3,904,701 | 9/1975 | Schultz et al. | 570/166 |
| 4,147,733 | 4/1979 | Fiske et al. | 260/653.4 |
| 4,766,258 | 8/1988 | Komatsu et al. | 570/168 |
| 5,008,474 | 4/1991 | Wairseveas et al. | 570/168 |
| 5,155,082 | 10/1992 | Tung et al. | 502/228 |
| 5,208,395 | 5/1993 | Elsheikh | 570/166 |
| 5,396,001 | 3/1995 | Peanstreau | 870/179 |

FOREIGN PATENT DOCUMENTS

| | | |
|---|---|---|
| A648783 | 12/1964 | Belgium . |
| 715612 | 8/1965 | Canada .................. 570/165 |
| 832502 | 1/1970 | Canada . |
| 1074434-A | 7/1993 | Canada . |
| 1069019a | 2/1993 | China . |
| 0 187 643 | 4/1989 | European Pat. Off. . |
| 637 579 A1 | 4/1993 | European Pat. Off. . |
| 0 547 930 A1 | 6/1993 | European Pat. Off. . |
| 0 606 482 A1 | 7/1994 | European Pat. Off. . |
| 0 637 579 al | 2/1995 | European Pat. Off. . |
| 0 676 386 A1 | 10/1995 | European Pat. Off. . |
| 0 693 469 A1 | 1/1996 | European Pat. Off. . |
| 48-16487 | 5/1973 | Japan . |
| 53-116304 | 10/1978 | Japan . |
| 228021 | 8/1994 | Japan .................. 570/167 |
| WO 94/22796 | 10/1994 | Japan . |
| 341788 | 6/1972 | Russian Federation . |
| 423789 | 4/1974 | Russian Federation . |
| 466202 | 4/1975 | Russian Federation . |
| WO94/22796 | 10/1994 | WIPO . |
| WO94/22797 | 10/1994 | WIPO . |
| WO94/23813 | 10/1994 | WIPO . |

OTHER PUBLICATIONS

Vogel "Practical Organic Chemistry" 3rd ed. 1957 pp. 92–95.
Harold R. Null, Phase Equilibrium In Process Design, *Wiley–Interscience*, 124–126, 1970.
Stanley M. Walas, Phase Equilibriua In Chem. Eng., *Butterworth Publishers*, 165–244, 1985.

*Primary Examiner*—C. Warren Ivy
*Assistant Examiner*—Lyman H. Smith

[57] ABSTRACT

A process is disclosed for producing 1,1-difluoroethane (HFC-152a) in a liquid phase by contacting chloroethene and hydrogen fluoride in the presence of a tin tetrahalide catalyst. The ability to reduce tar formation and increase volumetric productivity is also disclosed.

11 Claims, 1 Drawing Sheet

CONTINUOUS MANUFACTURE OF 1,1-DIFLUOROETHANE

FIELD OF THE INVENTION

The instant invention relates to a process for producing 1,1-Difluoroethane (HFC-152a) in a liquid phase by contacting chloroethene and hydrogen fluoride in the presence of a tin tetrahalide catalyst. A desirable aspect of the instant invention relates to a reduced rate of tar formation and an increased volumetric productivity.

BACKGROUND 1,1-Difluoroethane ($CHF_2CH_3$ or HFC-152a) can be manufactured by using either a liquid phase or gas phase process.

Elsheikh (U.S. Pat. No. 5,208,395, dated May 4, 1993) describes a gas phase process for producing HFC-152a from 1,1-dichloroethane and hydrogen fluoride in the presence of solid tin tetrafluoride on activated carbon.

Golubev et al. (Soviet Inventor Certificate No. 341788, dated Jul. 7, 1972) describe a liquid phase process for reacting chloroethene with hydrogen fluoride to form HFC-152a.

Guofei et al. (Chinese Patent Application Publication No. 1069019a) operate the liquid phase process to manufacture HFC-152a.

The disclosure of the aforementioned patents and published patent applications is hereby incorporated by reference.

SUMMARY OF THE INVENTION

In conventional processes for making HFC-152a, high boiling materials (commonly referred to as tars) are formed. Tars can interfere with catalyst activity, fill up reactor space, decrease the yield of the desired product, among other problems. It is known in the art that alkenes and alkynes, such as chloroethene, are prone to form tars. The instant invention relates to a process for making HFC-152a at high rates and yields while solving problems associated with conventional manufacturing processes such as tar formation.

The inventive process achieves high production rates of HFC-152a by using a catalyzed liquid phase process. This invention also relates to a reduced rate of tar formation by improving the dispersion of the starting material(s) in the liquid phase. Without wishing to be bound by any theory or explanation, it is believed that an improved dispersion functions to minimize the concentration of the starting materials at any given location within the reactor thereby inhibiting polymerization, i.e., tars.

An improved dispersion can be achieved by employing one or more of the following techniques: 1) vaporizing the starting material(s), 2) introducing the starting material into the reactor at a high velocity, 3) agitating the reaction mixture, 4) diluting the starting material prior to being introduced into the reactor, among other suitable means for enhancing the dispersion in the reactor contents. By improving the dispersion of chloroethene within the liquid phase of the reactor, the tar yield can be reduced to less than about 1% by wt. % of the chloroethene, while the conversion of chloroethene to 1,1-difluoroethane can be at least 99%.

CROSS REFERENCE TO RELATED APPLICATIONS

Figure 1:
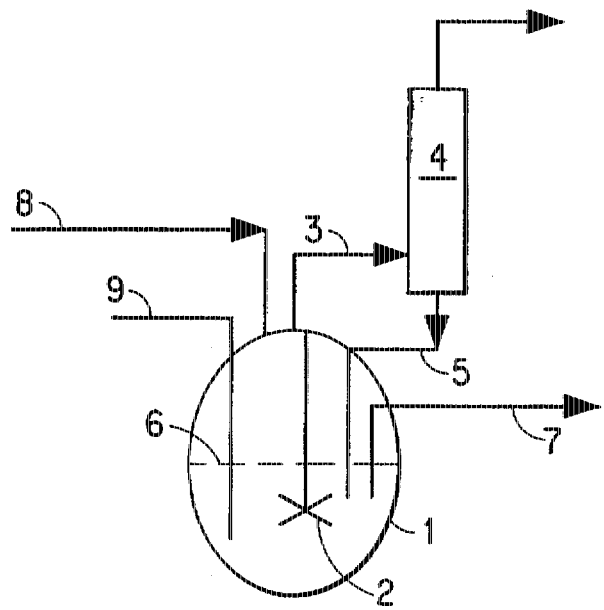
FIG. 1. is a schematic of the continuous process that can be used to practice one aspect of the invention.

The subject matter of this invention is related to copending and commonly assigned U.S. patent application Ser. No. 08/468,099 (Attorney's Docket No. CH-2511) entitled "Azeotropic or Azeotrope-like Compositions of Hydrofluoric Acid With Dihaloethanes", which was filed on Jun. 6, 1995, in the names of Maria Beug-Deeb et al.

The subject matter disclosed herein is also related to copending and commonly assigned U.S. patent application Ser. No. 08/476,770 (Attorney's Docket No. CH-2529) entitled "Two Step Process For Manufacturing 1,1-Difluoroethane", which was filed on even date herewith in the names of Mario Nappa et al.

This subject matter is also related to copending and commonly assigned U.S. patent application Ser. No. 08/480,068 (Attorney's Docket No. CH-2530) entitled "Manufacture of 1,1-Difluoroethane By Reactive Distillation", which was filed on even date herewith in the names of Wendel Cassel et al.

The subject matter of these applications is hereby incorporated by reference.

DETAILED DESCRIPTION

Hydrofluorocarbons (HFCs) such as 1,1-difluoroethane can be an environmentally acceptable replacements for certain chlorofluorocarbons (CFCs). 1,1-difluoroethane ($CHF_2CH_3$ or HFC-152a) may be employed alone or in blends as a refrigerant, cleaning agent, blowing agent for thermoplastic or thermoset foams, an aerosol propellant, a heat transfer media, gaseous dielectrics, power cycle working fluids, polymerization media, particulate removal fluids, carrier fluids, buffing abrasive agents, displacement drying agents, an intermediate for other fluorinated compounds such as vinyl fluoride, among other applications.

1,1-difluoroethane can be made by contacting chloroethene ($CH_2=CHCl$ or vinyl chloride) with a liquid phase comprising anhydrous hydrofluoric acid, e.g., typically the HF will contain less than about 20 ppm wt. % water, and at least one suitable catalyst. The inventive process can employ any suitable catalyst such as at least one member from the group of $AlCl_3$, $TaCl_5$ ($TaX_5$), $MoCl_5$, $TiCl_4$, $HSO_3F$, $SnCl_4$, $BF_3$, among others. The inventive process can employ commercially available vinyl chloride, e.g., 99.98% VCM (min). Intermediates or byproducts to this conversion may include at least one of 1-chloro-1-fluoroethane (HCFC-151a) and 1,1-dichloroethane (HCC-150a). HCFC-151a and HCC-150a. These intermediates or byproducts can be employed as an intermediate for producing fluorocarbon compounds, e.g., vinyl fluoride, 1,1,1-trichloroethane, mixtures thereof, among other compounds. Alternatively, such intermediates or byproducts can be recycled to the inventive process for making additional quantities of HFC-152a.

High production rates of HFC-152a can be achieved by using a catalyzed liquid phase process. By "high production rate", it is meant that chloroethylene feed rates of up to about 2 kg/kg-catalyst-hr. can be used. Such high production rates can also be achieved without significant formation of high boiling materials (commonly referred to as tars), e.g., typically less than about 1 wt. % tar is formed by the inventive process. By "high boiling materials" or "tars", it is meant to refer to one or more compounds characterized by being a high molecular weight, e.g., 1,000–30,000 average molecular weight, highly branched hydrocarbon with low levels of halides.

The inventive process achieves high production rates of HFC-152a by using a catalyzed liquid phase process. This invention also relates to a reduced rate of tar formation by improving the dispersion of the starting chloroethylene material in the catalyzed liquid phase. An improved dispersion can be achieved by employing one or more of the following techniques: 1) vaporizing the starting material(s), 2) introducing the starting material into the reactor at a high velocity, 3) agitating the reaction mixture, 4) diluting the starting material prior to being introduced into the reactor, among other suitable means for enhancing the dispersion in the reactor contents. By improving the dispersion of chloroethene within the liquid phase of the reactor, the tar yield can be reduced to less than about 1% by wt., while the conversion of chloroethene to 1,1-difluoroethane was at least 99%, e.g. about 96 to about 98 wt. % pure HFC-152a can be obtained.

Without wishing to be bound by any theory or explanation, it is believed that depending upon the process conditions the alkene and/or alkyne starting materials can form the HFC-152a product, an intermediate, and/or a tar. By operating under conditions that favor converting starting materials into the HFC-152a product, the rate of tar formation is decreased. By improving the dispersion of, for example, the gaseous starting material into the liquid mass within the reactor, it is also believed that contact between the liquid phase, e.g., predominately HF, and chloroethene is enhanced thereby maximizing formation of HFC-152a. Such an improved dispersion also minimizes the concentration of vinyl chloride within the reactor mass thereby reducing tar formation. Consequently, the improved contact or dispersion within the liquid phase favors formation of a low-tar HFC-152a product at high yields.

The rate of tar formation is defined as the weight of high boiling materials, i.e., tar, divided by the weight of starting material(s). The amount of high boiling materials includes both the tars that are soluble and insoluble in the liquid phase.

While any suitable conditions can be employed for maintaining a liquid phase, typically the phase is at a temperature of about 60° to about 125° C., and pressure of about 70 to about 290 psia.

Referring now to FIG. 1, FIG. 1 is a schematic of one aspect of the inventive HFC-152a process. A stirred tank reactor 1 is equipped with a mechanical agitator 2 and connected via conduit(s) 3 and 5 to a reflux column 4. The reflux column 4 can be of conventional design containing 8 to 30 stages. The column 4 is typically operated at a pressure of about 70 to about 290 psia, and reflux ratio of about 1 to about 20. Predetermined amounts of HF and catalyst, e.g., about 5 to at least about 35 weight % $SnCl_4$ in HF, are added via conduit 9 to the agitated reactor. The contents of the reactor are heated to a temperature of about 50 to about 150 deg. C., and brought to reflux at the desired operating pressures, e.g., about 70 to 290 psig. After the desired reflux flow is reached, both HF and chloroethene can be fed simultaneously and continuously through conduit 2 to the reactor.

Gas that is exiting from the reactor via conduit 3 enters the reflux column 4, which is typically operated at a molar reflux ratio between about 1 and 20. The gas stream leaving the reflux column 4 typically consists essentially of equimolar amounts of HFC-152a and HCl, e.g., less than about 5% HF and trace amounts of VCM, HCFC-151a and HCC-150a. Liquid returns via conduit line 5 from the bottom of the reflux column 4 to the reactor 1. The liquid from the bottom of the reflux column 4 typically contains high boiling intermediates, e.g., 151a, 150a, and HF.

The stream exiting reflux column 4 can also be purified and/or separated into its individual components. Purification of the stream leaving the reflux column can be performed in two distillation steps (not shown). The first distillation step can remove the HCl from the stream such that a F152a crude stream can be obtained that contains less than about 0.10 wt. % HCl. The second distillation step removes any unreacted intermediates and HF that can be recycled back to the reactor, e.g., a crude product stream can be obtained that contains about 99.9 wt. % HFC-152a on an acid free basis. The first and second distillation steps can be practiced by employing any suitable conventional distillation column. While the specific temperature and pressure within the distillation columns can vary widely depending upon equipment design, material composition, among other factors, when operating at a pressure of about 260 psig the temperature of the first column can range from –25° C. at the column top and 70° C. at the column bottom. In general, an increase in distillation pressure increases the temperature of the column bottom.

To reduce the formation of tars in the reactor 1, the starting material, e.g., chloroethene, is vaporized and transported via conduit 9 into the reactor 1, preferably below the surface of the liquid phase, e.g., about or below the level of the agitation mechanism as shown by item 6 is FIG. 1. Typically, the vaporized starting material is introduced into the reactor 1 at a rate of about 0.5 to about 2 lbs./hr.-lb catalyst. Chloroethene can be vaporized by being passed through a heated pipe, and is maintained at a temperature of least about 1° C. above its boiling point at the operating pressure. Typically, the chloroethene vapors leaving the heated pipe are maintained at a temperature of about 35° to about 115° C.

Tars can also be reduced by agitating the reaction mass. The reactor can be agitated by using a suitable means such as a propeller or turbine, among others. When the agitation means comprises a turbine, it is operated at a tip speed of about 100 to 1500 feet/minute. The agitation means functions to improve the dispersion of starting materials within reactor 1. The degree of agitation is defined by the power input by the agitator. Power is a function of agitator size, liquid density, and rotational speed of the agitator. For example, a 4 inch diameter impeller rotating at a speed of 500 rpm in a liquid having a density of 1,000 kg/meters cubed would be about 11.5 Watts (0.0308 HP).

To further reduce the rate of tar formation, the vaporized starting material, e.g., chloroethene, can be introduced into the liquid phase within the reactor by using a jet nozzle. The vaporized chloroethene is introduced into reactor 1 below the surface 6 of liquid phase. The nozzle increases the velocity of the starting material to about 30 to about 200 ft/sec. While any suitable nozzle can be employed, the aforementioned nozzle can be created by drilling a small orifice into a cap located on the end of the feed line. The size of the orifice, which is employed to cause an increase in starting material velocity, is a function of the operating pressure and temperature in the reactor and the feed rate of starting material. The starting material velocity is a function of flow rate, molecular weight, pressure, temperature and orifice diameter. For example, a nozzle having an orifice diameter of about 0.0625" that is supplying 1,1-dichloroethene at a rate of 5 lbs/hr at a pressure of about 160 psig and a temperature of about 90° C. can generate a velocity of about 42 ft/sec.

Tar concentration within the reactor can be controlled by periodically purging a quantity of the liquid reaction mass within reactor 1. For example, about 10% of the liquid mass can be withdrawn via conduit 7. The composition of the withdrawn mass can be determined by using known techniques. The purge will also withdraw catalyst from the reaction mass that can be replaced as desired via conduit 8.

Figure 2:
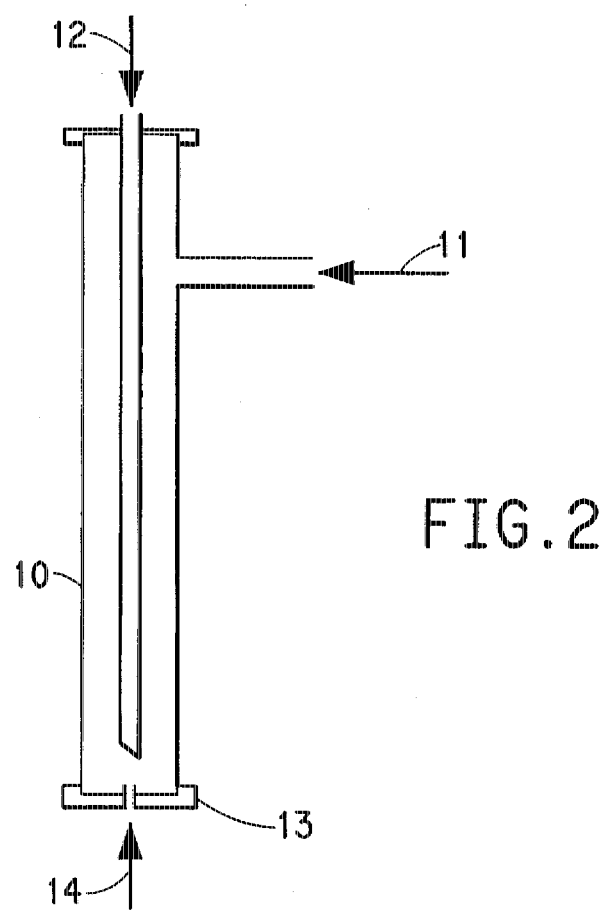
FIG. 2. is a cross-sectional schematic of a concentric feed pipe that can be used to practice an aspect of the invention.

Referring now to FIG. 2, FIG. 2 shows a cross-sectional schematic of a concentric feed pipe that can be employed as the aforementioned nozzle. The concentric structure of the nozzle allows for continuous flushing of the jet nozzle. The gaseous starting material, e.g., comprising chloroethane, is introduced into nozzle 10 via opening 11 that can be located at any suitable location. Nozzle 10 defines a central passageway 12 that can introduce liquid HF into the nozzle. The HF passageway 12 ends a short distance, e.g., about ⅛ to about 6 inches, from the end plate or cap 13. The central region of the planar surface of cap 13 defines an orifice 14. The structural relationship between the length of passageway 12 and cap 13 is such that the contact time between the gaseous chloroethene and the liquid HF is minimized. That is, this contact time is minimized prior to exiting orifice 14 into the liquid phase in the reactor, e.g., reactor 1 shown in FIG. 1.

It is believed that by increasing the fluid velocity of the starting material being introduced into the liquid phase within the reactor, the local mixing on the molecular level is increased and the amount of back diffusion of reactor mass into the conduit is decreased; thereby minimizing formation of tar. In other words, by introducing or injecting the starting material at a relatively high fluid velocity the conversion to HFC-152a product is favored over conversion to a tar.

In order to prevent the nozzle from becoming clogged, the nozzle can be flushed with liquid HF and/or another suitable liquid which does not interfere with the reaction. A suitable flushing liquid comprises 1,1-dichloro, 2,2,2-trifluoroethane.

In one aspect of the invention, one or more diluents can be added to the gaseous chloroethene starting material. The diluent can reduce the rate of tar formation in the reactor. For best results, the diluent typically has a normal boiling point less than 15° C. thereby permitting the diluent to be vaporized from the reactor, collected, and recycled. The diluent is typically either inert under the conditions of the reaction system, or is a material that already exists in the reaction system (and therefore does not contaminate the product). Consequently, the diluent avoids filling the reactor up and producing unnecessary waste material. Examples of suitable diluents comprise or consist of one or more of gaseous HCl, gaseous HFC-152a, gaseous HCFC-151a, and gaseous HF, among others. The diluent can range from 5 to 55% by volume of the VCM feed.

The reactor, distillation column, among other production equipment and associated feed lines, effluent lines and associated units should be constructed of materials resistant to HF and HCl. Typical materials of construction, well-known to the fluorination art, include common carbon steel, as well as stainless steels and the well-known high nickel alloys, such as Monel® nickel-copper alloys, Hastelloy® nickel-based alloys and, Inconel® nickel-chromium alloys.

Examples that illustrate certain aspects of the invention are given below. It is to be understood that these examples are merely illustrative and in no way are to be interpreted as limiting the scope of the invention defined in that appended claims.

EXAMPLE 1

Example 1 illustrates the effect of using a vapor or liquid starting material. Case 1 employs a vapor starting material whereas Case 2 employs a liquid starting material.

Case 1

Approximately 37.5 g of $SnCl_4$ were charged into a 600 ml Parr autoclave. The autoclave was then sealed and attached to a feed system capable of feeding liquid HF in a batch mode and feeding gaseous chloroethene continuously to the autoclave. Approximately 150 g of HF were then pumped into the autoclave. Vapor chloroethene was fed into the liquid phase within the reactor through a ¼ inch dip tube at a feed rate of about 50 cc/min to form a reactor mass. The reactor mass was agitated with a turbine impeller at a rate of 650 rpm while being maintained at a temperature of about 50 deg C. and a pressure of about 50 psi. Gas exiting from the reactor was passed through a reflux condenser, which was held at a temperature of about 4 deg C. by using a glycol/water recirculating bath. The offgas from the reflux condenser was analyzed by using gas chromatography, and was determined to contain about 98% by volume HFC-152a.

After operating the above process for about 18 hours, the volatile components were removed from the reactor by using a nitrogen purge. The solids remaining in the autoclave were drowned in water and filtered on a Teflon(TM) membrane filter to produce a filter cake. The filter cake was washed with 10% HCl, then with water and dried in a vacuum oven at a temperature of about 100° C. By using gravimetric techniques, it was determined that the tar formation rate was about 1.9 g tar per 100 g chloroethene.

EXAMPLE 1:CASE 2

Approximately 37.5 g of $SnCl_4$ and HF were charged to a 600 ml Parr autoclave substantially in accordance with the process described in Example 1:Case 1. Approximately 50 cc/min chloroethene vapor feed was condensed at a temperature of about 4 deg. C, and liquid chloroethane was added into the vapor space of the reactor through 1/16 inch tubing Reactor conditions were substantially identical to those employed in Example 1:Case 1. The offgas from the reflux condenser contained about 93% HFC-152a.

After operating this process for about 16 hours, the tar formation rate was calculated to be about 3.0 g tar per 100 g chloroethene.

A comparison of Example 1:Case 1 and Example 1:Case 2 illustrates that the rate of tar formation can be reduced by using a vapor starting material.

EXAMPLE 2

Example 2 illustrates the effects of agitating the reactor mass. Example 2:Case 1 was performed without agitation whereas Example 2:Case 2 agitated the reactor mass.

Case 1

A reactor was loaded with a liquid comprising approximately 20 weight % $SnCl_4$ in HF. The reactor was operated at a temperature of about 93° C. and a pressure of about 160 psig. Vaporized chloroethene was fed below the level of the liquid phase at a rate of about 0.59 lbs per hour/lb of $SnCl_4$, and a linear velocity of about 49 ft/sec. HF was fed into the reactor at a rate of about 0.38 lbs per hour/lb of $SnCl_4$.

To determine the rate of tar formation, samples were withdrawn from the reactor through a dip tube located below the liquid level, and collected into an aqueous caustic solution (comprising 18% KOH). The tar was then filtered from the caustic solution, dried in a vacuum oven at a temperature of about 125° C., and weighed. In addition, solid tars are collected from the bottom of the reactor after the reactor has been emptied. Total tar formation was calculated as the sum of the two tar measurement, and was expressed in amount of tar per amount of chloroethene fed. The total rate of tar formation was about 0.77 lbs/100 lbs. chloroethene.

EXAMPLE 2:CASE 2

The same reactor used in Example 2:Case 1 was loaded with a liquid phase comprising approximately 20 weight % $SnCl_4$ in HF. The reactor was operated at a temperature of about 91.5° C. and 160 psig. Vaporized chloroethene was fed into the liquid phase at a rate of about 0.70 lbs. per hour/lb. $SnCl_4$, and linear velocity of about 49 ft/sec. HF was fed into the reactor at a rate of about 0.45 lbs. per hour/lb. $SnCl_4$. The liquid phase or mass was agitated by using a 4-bladed turbine. The agitation speed was about 300 rpm. The total rate of tar formation was measured by using the process described in Example 2:Case 1, and was determined to be about 0.37 lbs. tar/100 lbs. chloroethene.

A comparison of Example:2 Case 1 and Example 2:Case 2 illustrates than by agitating the liquid phase tar formation can be reduced by about 50%.

The following is claimed:

1. A process for manufacturing 1,1-difluoroethane which comprises: providing a reaction vessel with a liquid phase of hydrogen fluoride containing an effective amount of catalyst; introducing a gas phase of vinyl chloride into said reaction vessel; reacting said vinyl chloride with said hydrogen fluoride while maintaining the temperature in said vessel from about 50° to 150° C. and the pressure from about 70 to 290 psia; recovering a gas stream comprising at least about 96% 1,1-difluoroethane and less than about 1% tar.

2. The process of claim 1 wherein said vinyl chloride further comprises a diluent.

3. The process of claim 2 wherein the diluent comprises HCl.

4. The process of claim 1 wherein the catalyst comprises at least one member from the group consisting of $SnCl_4$, $AlCl_3$, $TaCl_5$, $MoCl_5$, $TiCl_4$, $HSO_3F$, and $BF_3$.

5. The process of claim 4 wherein the catalyst comprises $SnCl_4$.

6. The process of claim 1 wherein the catalyst comprises about 5 to 35 wt. % of the liquid phase.

7. The process of claim 1 wherein the gas phase is introduced into the liquid phase at a velocity of about 30 to 200 ft/sec.

8. The process of claim 1 wherein the recovered 1,1-difluoroethane is about 96 to 98 wt. % pure.

9. The process of claim 1 wherein said process produces less than about 1.0 pound of tar per 100 pounds of vinyl chloride.

10. The process of claim 1 wherein said liquid phase is agitated.

11. A continuous process for making a 1,1-difluoroethane containing stream contacting a gas phase comprising vinyl chloride with a liquid phase comprising hydrogen fluoride and a catalyst comprising a tin halide to form a reaction mass, agitating the reaction mass, controlling tar concentration in said reaction mass by purging a portion of the reaction mass, introducing additional quantities of said catalyst to compensate for any quantity removed during said purging, recovering a gas phase product from the reaction mass, distilling the product, recovering 1,1-difluoroethane.

* * * * *